United States Patent
Goetz et al.

(10) Patent No.: US 9,918,839 B2
(45) Date of Patent: Mar. 20, 2018

(54) DEVICE INTENDED TO BE ATTACHED TO OR INTERCONNECTED WITH A CATHETER, CATHETER AND METHOD

(75) Inventors: Wolfgang Goetz, Regensburg (DE); Hou-Sen Lim, Singapore (SG)

(73) Assignee: VENUS MEDTECH (HANGZHOU), INC., Hangzhou (CN)

( * ) Notice: Subject to any disclaimer, the term of this patent is extended or adjusted under 35 U.S.C. 154(b) by 240 days.

(21) Appl. No.: 13/823,648

(22) PCT Filed: Sep. 14, 2011

(86) PCT No.: PCT/EP2011/004605
§ 371 (c)(1),
(2), (4) Date: May 22, 2013

(87) PCT Pub. No.: WO2012/034685
PCT Pub. Date: Mar. 22, 2012

(65) Prior Publication Data
US 2013/0245752 A1 Sep. 19, 2013

Related U.S. Application Data

(60) Provisional application No. 61/383,351, filed on Sep. 16, 2010.

(30) Foreign Application Priority Data

Sep. 14, 2010 (DE) .................. 10 2010 037 529

(51) Int. Cl.
*A61F 2/24* (2006.01)
*A61F 2/95* (2013.01)

(52) U.S. Cl.
CPC ............. *A61F 2/2439* (2013.01); *A61F 2/95* (2013.01); *A61F 2002/9505* (2013.01); *A61F 2002/9511* (2013.01); *A61F 2250/006* (2013.01)

(58) Field of Classification Search
CPC ............................. A61B 17/00; A61F 2/2439
(Continued)

(56) References Cited

U.S. PATENT DOCUMENTS 4,585,000 A * 4/1986 Hershenson .......... A61M 29/02
604/108
5,242,452 A * 9/1993 Inoue ........................ A61F 2/07
606/108
(Continued)

FOREIGN PATENT DOCUMENTS

CN 101426452 A 5/2009
DE 10 2006 057 216 A1 6/2007
(Continued)

OTHER PUBLICATIONS

International Search Report dated Apr. 3, 2012, issued in counterpart International Application No. PCT/EP2011/004605.

*Primary Examiner* — Alexander Orkin
(74) *Attorney, Agent, or Firm* — Hamre, Schumann, Mueller & Larson, P.C.

(57) ABSTRACT

A device is intended to be attached to or interconnected with a medical implant, and intended to be attached to or interconnected with a catheter. The catheter is intended for implanting the implant. A catheter is suited for receiving at least one such device and a method provides a delivery implement with an implant detachably disposed in the device.

21 Claims, 3 Drawing Sheets

(58) Field of Classification Search
USPC ..... 623/1.11, 1.12, 2.11; 606/108, 191, 192, 606/194, 195, 198
See application file for complete search history.

(56) References Cited

U.S. PATENT DOCUMENTS

| | | | | |
|---|---|---|---|---|
| 5,554,183 | A | | 9/1996 | Nazari |
| 5,562,603 | A | * | 10/1996 | Moll ................ A61B 17/0218 600/204 |
| 5,713,948 | A | * | 2/1998 | Uflacker ................ A61F 2/07 606/194 |
| 5,957,929 | A | * | 9/1999 | Brenneman ............ A61F 2/92 606/1 |
| 5,976,179 | A | * | 11/1999 | Inoue .................. A61F 2/07 606/194 |
| 6,866,679 | B2 | | 3/2005 | Kusleika ............... A61F 2/95 606/108 |
| 7,041,132 | B2 | * | 5/2006 | Quijano ............. A61F 2/2412 623/2.11 |
| 7,771,463 | B2 | * | 8/2010 | Ton .................... A61F 2/88 623/1.11 |
| 2003/0220680 | A1 | * | 11/2003 | Kashyap ................ A61F 2/95 623/1.11 |
| 2004/0015224 | A1 | * | 1/2004 | Armstrong ............. A61F 2/95 623/1.12 |
| 2005/0288764 | A1 | * | 12/2005 | Snow ................... A61F 2/95 623/1.11 |
| 2007/0088431 | A1 | * | 4/2007 | Bourang ............. A61F 2/2433 623/2.11 |
| 2007/0168014 | A1 | * | 7/2007 | Jimenez ................ A61F 2/95 623/1.12 |
| 2007/0203561 | A1 | * | 8/2007 | Forster ............. A61F 2/2418 623/1.11 |
| 2008/0082158 | A1 | * | 4/2008 | Tseng .................. A61F 2/07 623/1.13 |
| 2010/0049293 | A1 | * | 2/2010 | Zukowski ............. A61F 2/07 623/1.11 |
| 2011/0040366 | A1 | | 2/2011 | Goetz et al. |

FOREIGN PATENT DOCUMENTS

| | | |
|---|---|---|
| DE | 10 2008 012 113 A1 | 9/2009 |
| DE | 10 2008 013 381 A1 | 9/2009 |
| JP | 2009-528089 A | 8/2009 |
| WO | 2011/101136 A1 | 8/2011 |

* cited by examiner

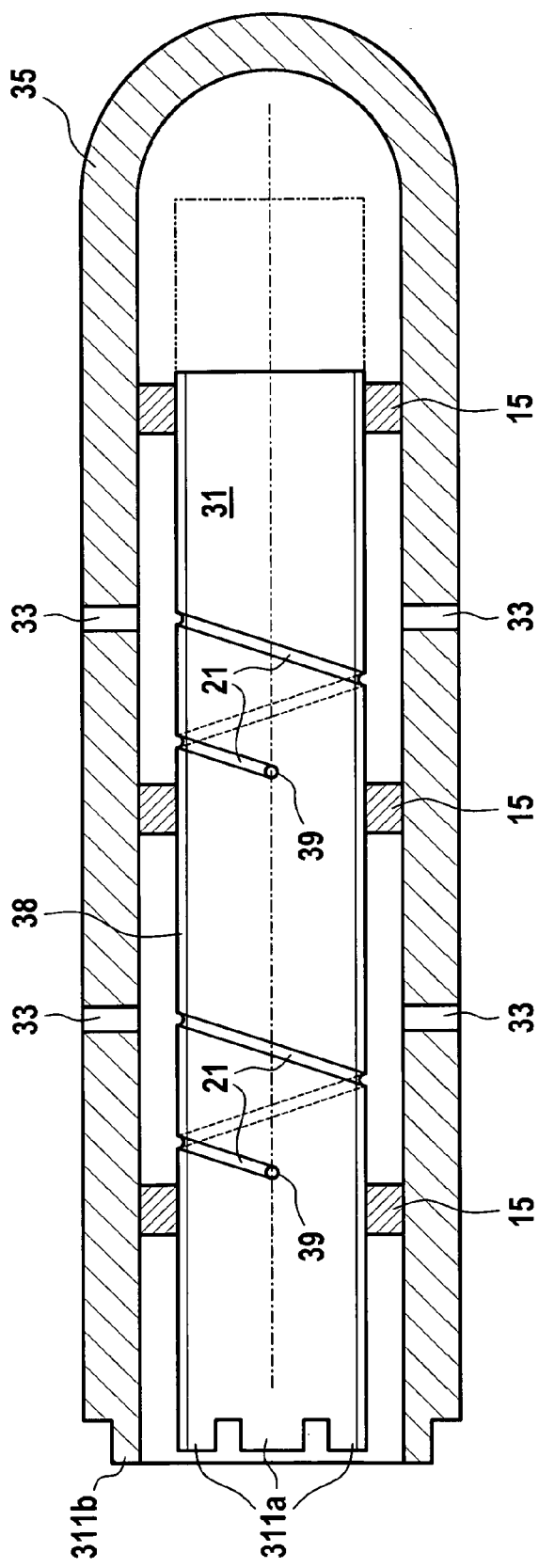
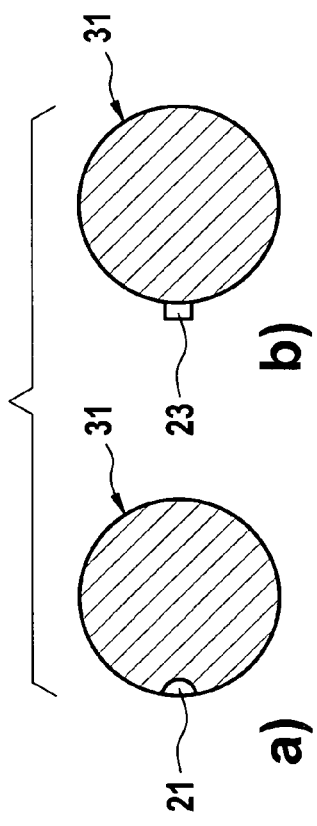
Fig. 3
Fig. 4

DEVICE INTENDED TO BE ATTACHED TO OR INTERCONNECTED WITH A CATHETER, CATHETER AND METHOD

CROSS-REFERENCE TO RELATED APPLICATIONS

This application is filed under 35 U.S.C. 371 as a U.S. national phase application of PCT/EP2011/004605, having an international filing date of 14 Sep. 2011, which claims the benefit of U.S. Provisional Application No. 61/383,351, having a filing date of 16 Sep. 2010, and German Patent Application No. 10 2010 037 529.2, having a filing date of 14 Sep. 2010, all of which are hereby incorporated by reference.

TECHNICAL FIELD

The present invention relates to a device intended to be attached to or interconnected with a catheter as described below. The invention further relates to a catheter suited for receiving at least one such device and a method as disclosed herein.

BACKGROUND

In a number of patients, certain body functions have to be carried out or supported by means of implants. In order to facilitate the delivery of the implants to the implantation site within a patient's body, the implants are often attached to mechanical devices such as, for example, catheters.

It is one object of the present invention to provide a device and a method for attaching or interconnecting a medical implant with a catheter. According to a further aspect, a catheter comprising at least one such device and a method are provided.

The object of the invention is solved by means of a device as set forth herein.

SUMMARY

In particular, the device according to the invention is intended to be attached to or interconnected with a medical implant and is intended to be attached to or interconnected with a catheter. The device comprises a portion intended for folding and/or unfolding the implant.

Embodiments can include one or more of the following features.

The device according to the invention can be temporarily or permanently or detachably attachable to or interconnectable with the medical implant. The device according to the invention can be temporarily or permanently or detachably attachable to or interconnectable or connected, respectively, with the catheter. The catheter is intended for implanting the implant.

The term "catheter"—in the sense of the present invention—is used by way of example for any delivery or advancing implement or device for advancing or delivering the medical implant to the implantation site. Hence, the term is not to be understood to relate only to catheters—rather, any suitable device adapted and/or intended or construed for advancing an implant to its implantation site is contemplated and may, thus, also be referred to as a catheter within the meaning of the present invention.

The device can be mainly or partly tube-shaped. As such, the device can have a circular or oval cross-section. However, the device may also have any other cross-section apt for establishing a connection between the device and the catheter according to the invention.

As regards the implant, the device according to the invention does not have to be designed in a particular way as long as the implant can be temporarily or permanently or detachably fixed at or onto the device according to the invention.

In some embodiments according to the invention, the device according to the invention detachably comprises the implant.

The implant can be of any type that is known to a person skilled in the art for supporting or carrying out functions of a patient's body. Examples include implants such as heart valves, substitutes or replacement of heart valves, stents for holding vessels or other body tubes open, and the like.

The implant may be of an expandable and/or (again) foldable or collapsible, respectively, type as is, for example, described together with the implementation thereof as such in great detail in WO 2008/029296 A2 ("Minimally invasive heart valve replacement," filed on Feb. 15, 2007) to the inventors of the present invention, and also in WO 2009/109348 A1 ("Stent, welcher vom expandierten Zustand kontrolliert erneut im Durchmesser verringerbar ist," filed on Mar. 2, 2009) also to the inventors of the present invention.

In certain embodiments according to the invention of the device, the portion intended for folding or unfolding the implant is arranged rotatably, in particular around a longitudinal axis of the device according to the invention or of the catheter.

The rotatability can relate or be relative, respectively, to the surroundings, an exterior, an outer layer, or the like of the device according to the invention.

The portion intended for folding or unfolding the implant can be supported within the device by means of a bearing, e.g., a pivot bearing.

The portion can be provided in one single component with the first portion of the means for attaching or interconnecting described further below or can be provided in force connection in any other way such that both portions are able to rotate only commonly.

The portion for folding and/or unfolding the implant can be cylindrical or a rotationally symmetrical portion or comprise such a portion.

The portion for folding and/or unfolding the implant may have openings intended for guiding strings or threads therethrough.

The portion intended for folding or unfolding the implant can consist of or comprise another material than a thread or string, respectively, material.

It can have another form than a thread or string, respectively, form.

The portion can be provided and intended for winding a thread or a string thereon, the thread or string being intended for folding and/or unfolding the implant.

The portion intended for folding or unfolding the implant can be detachably interconnected with the device.

In some embodiments, the portion intended for folding or unfolding the implant can be provided and/or intended not to be separated or released from the device by cutting.

In certain embodiments, the portion intended for folding or unfolding the implant may not contact the implant in the state of use of the device.

The portion intended for folding or unfolding the implant is completely separated from the implant by means of an outer component or layer of the device in the state of use of the device in some embodiments according to the invention.

In certain embodiments according to the invention of the device, the portion is interconnected with a portion of the means for folding and/or unfolding the implant. This connection can be an interlooping connection, a screwing connection, a sticking connection, or the like.

In some embodiments according to the invention of the device, the portion comprises a guiding structure.

The guiding structure can be provided at an outer surface of the portion.

The guiding structure can comprise or consist of one or more channels or grooves, respectively, or recesses that are intended for winding the means for folding and/or unfolding the implant, e. g., in form of one or more threads or strings, respectively.

The guiding structure can comprise or consist of one or more fins or noses or lugs, respectively, that are intended for winding the means for folding and/or unfolding the implant, e. g., in form of one or more threads or strings, respectively.

The device according to the invention can further comprise a displacing means or an advancing means (or mechanism) by which the portion for folding and/or unfolding the implant can be moved forwards or backwards during its rotation around its longitudinal axis within the device according to the invention or a portion thereof.

In some embodiments, it is contemplated to actuate the displacing mechanism or the advancing mechanism or a corresponding mechanism intended for advancing, retracting or displacing the portion intended for folding and/or unfolding the implant by hand only. In other embodiments, a motor or the like is provided and intended to be used (solely or auxiliary) for advancing or displacing the portion intended for folding and/or unfolding the implant.

In certain of the embodiments in which such a motor is provided, the motor or main parts of it can be located, for instance, at or near the tip or in or at a tip portion of the catheter. In other embodiments, the motor or main parts of it can be located at the catheter's handle.

In some embodiments, the implant is foldable and/or unfoldable and comprises means for folding and/or unfolding the implant.

In certain embodiments, the implant is intended to be attached to or interconnected with the device by means of crimping or folding. That is, the device is intended to have the implant crimped or folded, respectively, thereon, or the implant has already been crimped or folded, respectively, onto the device.

The folding and/or unfolding means are guided around certain portions of the implant that can be tightened or released.

The folding and/or unfolding means can be provided at or at least in connection with the implant such that it is or they are, respectively, operatively connected with the implant. The folding and/or unfolding means can be arranged such that it or they, respectively, can contribute to or effect the folding and/or unfolding of the implant which is attached to the device according to the invention. The folding and/or unfolding of the implant by means of the folding and/or unfolding means can be effected when a force, a tension or stress or strain is applied or put, onto the folding and/or unfolding means or rather released from the folding and/or unfolding means. Such a tension, stress or strain can, for example, be induced or generated by an actuating device (e. g., a pulling device) which can be operated by a user.

The means for folding and/or unfolding the implant can pass through an inner space of the device. The folding and/or unfolding means of the implant can be arranged such that they leave the device according to the invention through at least one opening of the device. Such an opening may be provided at one end of the device according to the invention. However, the folding and/or unfolding means can leave the device according to the invention also at any other suitable position and/or re-enter therethrough. The folding and/or unfolding means can leave the device according to the invention all through the same opening, however, some of the folding and/or folding means can also leave the device according to the invention through different openings and/or re-enter therethrough.

In some embodiments according to the invention, the folding and/or unfolding means can comprise one or more reins or threads or strings or can consist thereof.

In particular embodiments according to the invention, the folding and/or unfolding means are not identical to the device.

In some embodiments according to the invention, the device is not intended to be implanted itself or to remain within the patient's body after the implantation procedure has been finished.

In certain embodiments according to the invention, the device is intended to be separated from the implant after the implantation procedure has been finished.

In some embodiments according to the invention, the device is configured to be separatable from the implant during normal use of the device. In certain embodiments according to the invention, the device is not permanently attached to the implant or linked to it.

In some embodiments according to the invention, the device is arranged within a central part or through-hole of the implant.

In certain embodiments according to the invention, the device according to the invention and/or the catheter comprise attaching or interconnecting means. Such attaching or interconnecting means are intended and provided for attaching or interconnecting the device according to the invention to or with, respectively, a catheter. The attaching or interconnecting means can assist or support the attachment or interconnection of the device according to the invention with or to, respectively, the catheter.

In some embodiments according to the invention, the means for attaching or interconnecting comprises a first section which is arranged rotatably in or at the device, in particular around a longitudinal axis of the device according to the invention or of the catheter.

In certain embodiments according to the invention, the first section is preferably rotatably supported in or at the device.

In some embodiments according to the invention, the means for attaching or interconnecting comprises a second section which is not arranged rotatably in or at the device, in particular not around a longitudinal axis of the device according to the invention or of the catheter.

The rotatability can relate to the surroundings, an exterior, an outer layer, or the like of the device according to the invention.

Examples for the first and the second section include lugs or noses or the like, but also recesses or notches, toothings or coggings, dogs, tooth or gear wheel structures, clip connections, plug-in connections, or the like. However, the device does not have to comprise particularly formed geometrical shapes.

Everything that was said herein about the first section of the means for attaching or interconnecting may undiminishedly also apply for the third section. This is, however, not mandatory.

Everything that was said herein about the second section of the means for attaching or interconnecting may undiminishedly also apply for the fourth section. This is, however, not mandatory.

In some embodiments according to the invention, the first and the second section are present on or in or at the device according to the invention.

In some embodiments according to the invention, the third and the fourth section are present on or in or at the catheter according to the invention.

In order to establish a preferably tight or firm connection between, e. g., the first and the third section and/or between the second and the fourth section, the device according to the invention can, for example, comprise male faces or terminals at the first and/or the second section and the catheter can comprise female faces or terminals at the third and/or the fourth section or vice versa. As such, the connection between the device according to the invention and the catheter can resemble or be one plug-in connection or two plug-in connections.

In certain embodiments according to the invention, the device according to the invention is a catheter tip. During preparation of implanting the implant attached to the device according to the invention by means of the catheter, the device, the catheter tip or the like can be attached to or interconnected with the catheter by merely slipping or snapping on the catheter tip onto the catheter in situ, for example, in the operating room or theatre.

In some embodiments according to the invention, the catheter according to the present invention is suited and/or configured or prepared for receiving at least one such device according to the invention.

In certain embodiments according to the invention, the catheter according to the invention comprises at least one device according to the invention.

The catheter can be mainly or partly tube-shaped. As such, the catheter can have a circular or oval cross-section. However, the catheter can have every other cross-section apt for establishing a connection between the catheter and the device according to the invention. The catheter can be a catheter shaft.

According to the present invention, a method according to the invention serves for loading or providing a delivery implement with an implant before implantation, wherein the method comprises attaching or fixing a device according to the invention comprising an implant onto a delivery implement.

The attachment or fixation of the device according to the invention at or onto the delivery implement such as a catheter, in particular a catheter according to the invention, can be performed at any desired or required point of time. In some embodiments according to the invention, the device is attached or fixed to the delivery implement in the operation room or theatre or at the bedside.

Along with advantages that are obvious to the skilled one, the embodiments may provide one or more of the following advantages.

By using the device according to the invention, the present invention provides a simple option for attaching or interconnecting an implant to or with a catheter at any desired or required point of time, in particular in situ in the operating room just before implanting the implant.

As medical implants can also partly or entirely consist of living tissue, such as, for example, pig heart valves, it may be recommended to keep the living tissue in fluid environment during storage or transport.

However, due to its mechanical structure, the catheter as a whole should not be stored or transported under wet conditions.

With the present invention, it is advantageously possible to store and/or transport the implant and the catheter separate from each other in the respective best suitable environments.

In some embodiments according to the invention, it is possible to assemble them for the purpose of implanting in a relative short time and in an uncomplicated manner. For example, in certain embodiments of the invention, a cumbersome assembling of strings and implant right before implantation, e.g., at the bedside, can advantageously be avoided.

In this way, it is advantageously possible to store and/or transport the catheter in a, for example, dry environment suitable for the sensitive mechanical structure of the catheter; and to store and/or transport the implant under wet or humid conditions in order to keep the biological tissue in a humid condition. Thus, possible damages of the mechanical structure of the catheter can advantageously be avoided. The biological tissue does not dry out.

The device according to the invention can be designed or constructed such that it is not susceptible by fluids such as, for example, liquids surrounding the implant or is damaged or destroyed by those. As such, it is advantageously also possible to interconnect the device according to the invention and the implant before storage or transportation. Due to the separation of catheter and device (tip of the catheter, for example), both the catheter and the device can be manufactured from different materials, in different processes and the like. Each can thus be manufactured to its best and independently from the other part.

Due to the attaching or interconnecting means of the device according to the invention, it is advantageously possible to establish or achieve a simple and uncomplicated connection between the device and the catheter.

As, according to the invention, the means for folding and/or unfolding the implant are interconnected with the portion for folding and/or unfolding the implant provided in the device and as the means for folding and/or unfolding are thus provided at the device alone and not also at the catheter, the means for folding and/or unfolding can advantageously be kept short.

Moreover, due to their shortness, the means for folding and/or unfolding do not have to be guided through an interior of the catheter to the hand of a surgeon as it has to be the case in other solutions of the applicant of the present application as well. The present solution is thus advantageously characterized in that the means for folding and/or unfolding do not have to be diverted or deflected, respectively, at all or only less, cannot experience any shear forces, experience less friction, and the like and the possibility of being displaced, entangled or the like is advantageously reduced.

Another advantage can be that, due to shorter means for folding and/or unfolding the implant, a shorter range of move is required for the mechanism used. Thus, for the example of the thread as a means for folding and/or unfolding the implant it is known that the thread is subjected to a lengthening generated due to mechanical stress. This lengthening resulting in a reduced precision of the function of the entire mechanism may advantageously be prevented or, however, significantly reduced with respectively short threads as are possible according to the invention.

Another advantage of the present invention is that, due to their short design, less forces act on the means for folding and/or unfolding that do not have to be diverted around curves, bendings, and the like. This particularly applies at bending portions of the means and/or the device or the catheter, respectively. The means such as, e. g., the one or more threads can be manufactured thinner, more simply, cheaper. This advantageously further allows for a cutting device for cutting the threads after a successful implantation of the implant being designed in a more simple, smaller and/or cheaper way.

A still further advantage of the present invention is the omission of the requirement of having to connect the means for folding and/or unfolding the device that can, for example, be threads or strings, respectively, with means for their operation that can be provided in the catheter after attaching the device at the catheter. A connection of the means for folding and/or unfolding of, e.g., the threads with the catheter is not required. It is sufficient for the present invention to connect the device with the catheter. A further connection is not required. In this way, in particular a connection of threads of the device with threads of the catheter or the like which can be time-consuming and cumbersome can be omitted. The latter can advantageously contribute to maintaining the required sterility.

According to the invention, it is thus possible that the means for folding and/or unfolding the implant are solely present in the device, e. g., at the catheter tip. They do not have to extend across the entire catheter. In this way, the catheter does also not have to be designed such that the means can penetrate therethrough.

Another advantage is that—in a correspondingly designed guiding structure that can extend, for example, spirally or helically along the portion for folding and/or unfolding the implant—a winding path of the means for folding and/or unfolding the implant that is designed in form of a thread in one embodiment can disperse or extend, respectively, along the longitudinal axis of the portion for folding and/or unfolding the implant. Thus, an only small space within the device according to the invention, for example, between an outer sheath and the portion for folding and/or unfolding the implant rotatably supported therein is sufficient for winding the thread as close as possible at or around the portion for folding and/or unfolding the implant. In this way, the device according to the invention can advantageously be designed having a smaller diameter. The same advantage can be obtained by providing an advancing mechanism or a displacing mechanism.

Other aspects, features, and advantages will be apparent from the description, figures and claims. In the following, the invention is further explained by means of the figures of the drawing. However, the invention is not limited to the examples explained by means of the figures.

BRIEF DESCRIPTION OF THE DRAWINGS

FIG. 3 schematically shows a device according to the invention of a second embodiment designed as a catheter tip in a longitudinal section; and FIG. 4a, b show the portion for folding and/or unfolding the implant in different embodiments in cross-section.

DETAILED DESCRIPTION

Figure 1:
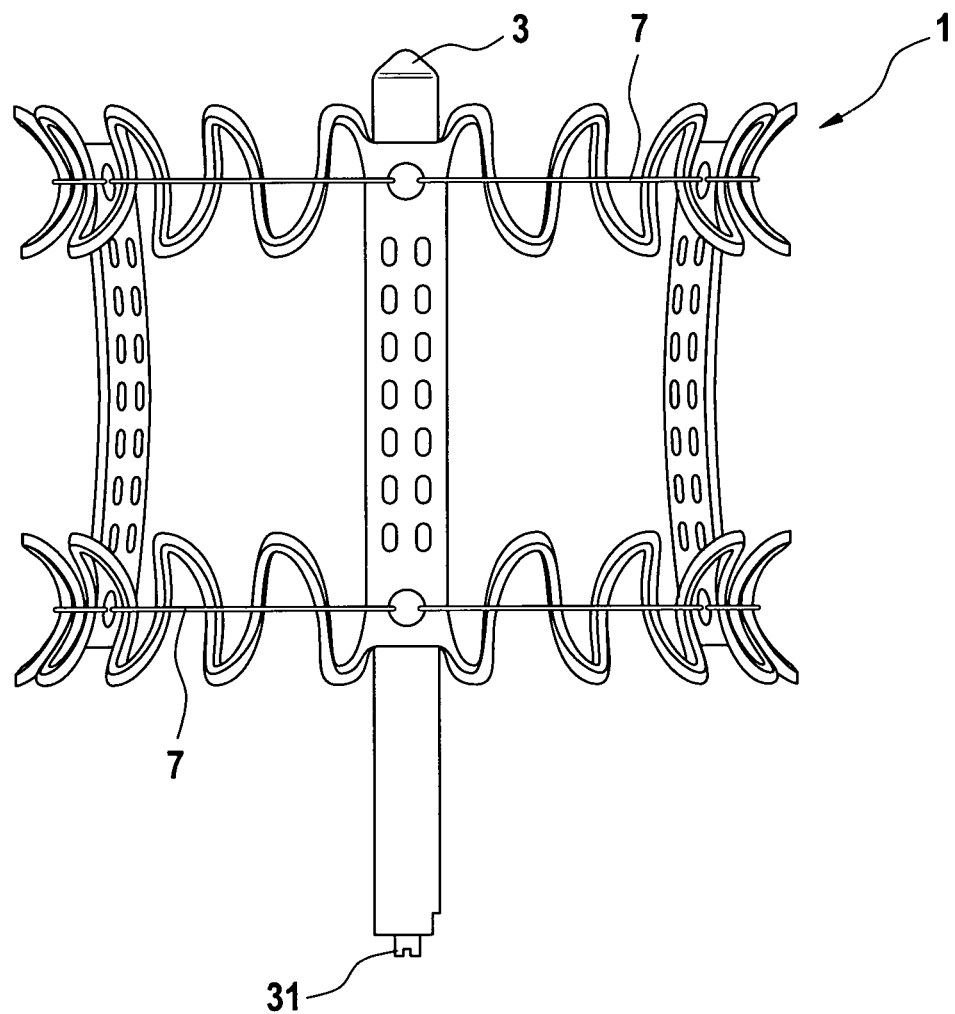
FIG. 1 shows a device according to the invention comprising an implant.
Figure 1:
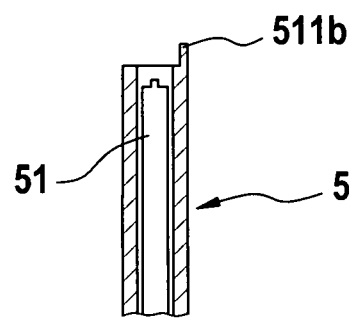

FIG. 1 shows an implant 1, viewed from the side, in an expanded state. The implant 1 is connected to a device 3 according to the invention. The device 3 is designed in form of a catheter tip.

At the lower end of FIG. 1, a part of a catheter 5 is shown. The catheter 5 is detached from the device 3.

The device 3 comprises a portion 31 for folding and/or unfolding the implant 1. The catheter 5 comprises a heart or a cord 51 and a fourth section 511b for its connection with the device 3.

The device 3 and/or the implant 1 comprise first folding and/or unfolding means 7. The folding and/or unfolding means 7 can be embodied as strings.

Figure 2:
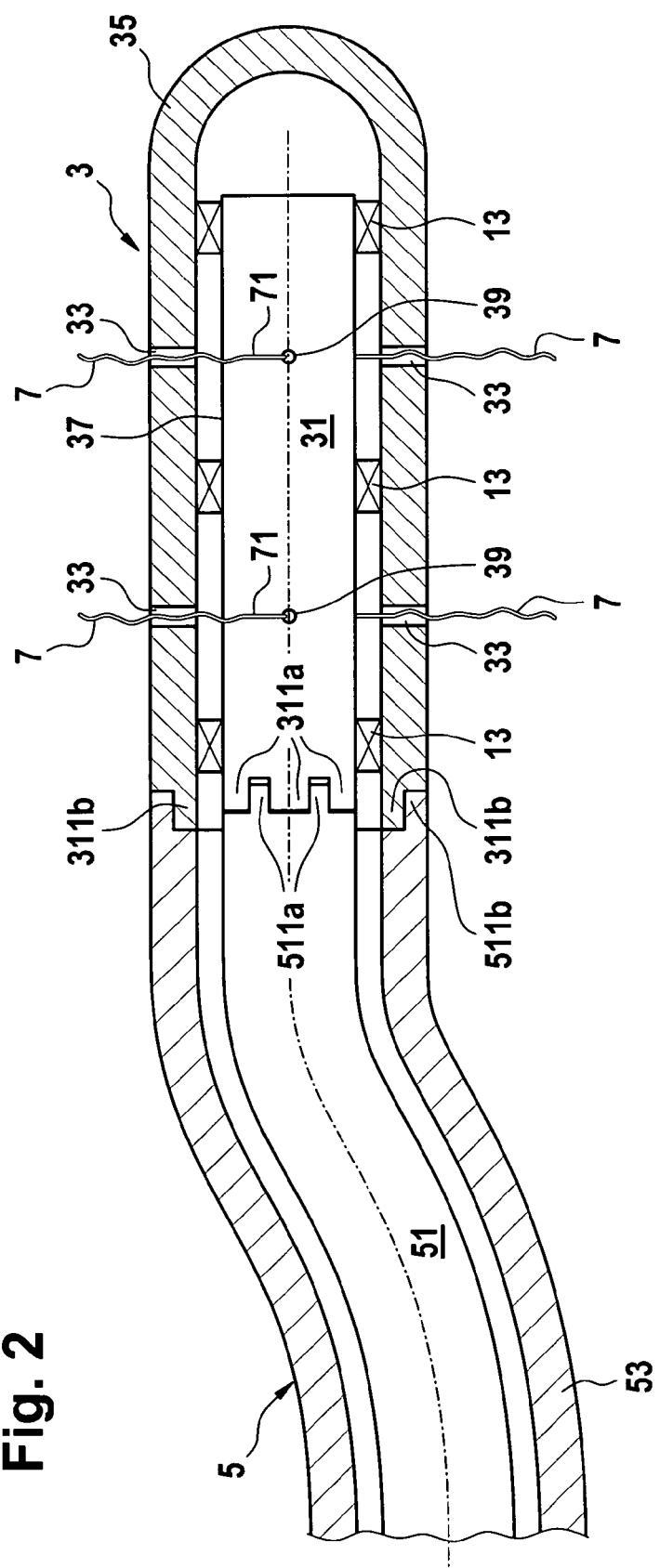
FIG. 2 schematically shows a part of a catheter comprising a device according to the invention of a first embodiment designed as a catheter tip in a longitudinal section.

FIG. 2 shows a device 3 according to the invention having an inner portion 31 for folding and/or unfolding the implant that is rotatably supported on three bearings 13 in an outer sheath 35. The device 3 which is shown in a first embodiment in FIG. 2 is connected with a flexible catheter 5 in the representation of FIG. 2. The catheter 5 comprises a flexible cord 51 or heart rotatably supported in a catheter sheath 53. In the representation of FIG. 2, the cord 51 can be rotated within and relative to the catheter sheath 53. This can be effected by means of respective bearings (not shown in FIG. 2 and not even mandatorily required). However, instead of those bearings, there can be provided corresponding geometrical embodiments of the catheter 5 and/or corresponding surface characteristics or treatments of the cord 51 and/or of the inner surface or the periphery surface, respectively, of the catheter sheath 53.

In the example of FIG. 2, the outer sheath 35 as well as the catheter sheath 53 are interconnected by means of a second section 311b and a fourth section 511b both embodied across the entire periphery of the sheath 35 and the catheter sheath 53. However, in other embodiments according to the invention, the second section 311b and the fourth section 511b can also solely be provided across certain portions of the periphery.

In the example of FIG. 2, the second section 311b and the fourth section 511b are plug-in connections that do not permit a rotation of the outer sheath 35 of the device 3 relative to the catheter sheath 53 of the catheter 5 during normal use of the device 3 and/or the catheter 5. Thus, the device 3 as a whole can only be rotated around its longitudinal axis even if the catheter 5 is rotated around the longitudinal axis thereof in at least the portion receiving the device 3.

The opposite applies for portion 31 for folding and/or unfolding the implant (which is not shown in FIG. 2). The portion 31 is arranged rotatably within the outer sheath 35 of the device 3 by means of the bearings 13. The portion 31 can be actuated by means of a rotational move of cord 51—relative to the catheter sheath 53 of the catheter 5—to perform a rotation around the longitudinal axis of portion 31 indicated by the dot dash line.

Such a coupling between cord 51 of the catheter 5 and portion 31 for folding and/or unfolding the implant of device 3 is, for example, possible by means of the first and third sections 311a and 511a represented in FIG. 2. The first section 311a and the third section 511a can be frictional and/or form closure connection devices.

It can be further seen from FIG. 2 that threads or strings that represent examples for the means 7 for folding and/or unfolding the implant not shown in FIG. 2 are guided from an interior of the device 3 through openings 33 to an exterior of the outer sheath 35 in order to be in contact with the implant not shown here. As the threads are connected with the portion 31 for folding and/or unfolding the implant in a portion 71 thereof (for example, by means of interlooping, sticking or the like, in each case by means of a frictional and/or form closure connection), the threads are wound up during the rotational move of the portion 31 around the longitudinal axis thereof around an outer surface 37 or an outer periphery, respectively, of the portion 31 for folding and/or unfolding the implant.

FIG. 3 shows a device 3 according to the invention according to a second embodiment hereof. The embodiment shown in FIG. 3 differs from the embodiment of FIG. 2 at least in that the portion 31 for folding and/or unfolding the implant comprises grooves 21 that are wound spirally or helically along the longitudinal axis (the dot dash line of FIG. 3) around the portion 31 for folding and/or unfolding the implant. A thread (as an example for a means 7 for folding and/or unfolding the implant which is also not shown in FIG. 3), that is, for example, attached at an attachment site 39 of the portion 31 for folding and/or unfolding the implant that is not shown in FIG. 3, may—after having been wound around the portion 31, be provided within the outer sheath 35 such that the thread is received within the groove 21. The thread thus extends across the longitudinal axis of the portion 31 for folding and/or unfolding the implant. In this way, an agglomeration of thread material at a closely limited periphery portion of the portion 31 due to winding the thread upon folding the implant is prevented. A space between portion 31 and outer sheath 35 can thus be embodied marginally or small.

In order to favour such a winding of the thread along the longitudinal extension of the portion 31, in the embodiment shown in FIG. 3 opposite to the device 3 according to the invention of FIG. 2, the portion 31 is embodied having a worm or thread 38 which is engaged with engagements 15. In this way, the portion 31 can be displaceable into the position indicated by the dot dash line to the right, relative to the plane of projection of FIG. 3, during its rotation within the outer sheath 35 of the device 3. In the embodiment of FIG. 3, the worm or thread 38 and the engagements 15 act together as one example of an advancing mechanism or a displacing mechanism. In FIG. 3, the engagements 15 replace the bearing 13 represented in the embodiment shown in FIG. 2. Alternatively, instead of the engagements 15 a worm can be provided at the outer sheath 35 as well. Moreover, the engagements 15 can alternatively be provided on the portion 31.

It is further obvious that it is contemplated according to the invention to provide an engagement on an outer surface of the portion 31 and a worm as being part of the outer sheath 35 instead of the outer worm or thread 38 of the portion 31 and the engagement 15. The present invention encompasses both embodiments.

By means of worm and/or engagements, a mechanism for effecting a longitudinal displacement of the portion 31—relative to the outer sheath 35—is given in the embodiments of FIG. 3. However, the said can of course be embodied in another way than the one given in the example of FIG. 3.

It is obvious that the provision of grooves 21 can be provided or can also not be provided independently from the provision of a mechanism for effecting a longitudinal displacement of the portion 31, relative to the outer sheath 35 in the device 3.

Furthermore, a person skilled in the art will recognize that a fin 23 can be provided instead of groove 21 as shown in FIG. 3 and as can also be seen in FIG. 4a in the cross-section of portion 31 along which, for example, the thread can be guided as a means 7 for folding and/or unfolding the implant.

As is obvious to the skilled person, the present invention is, of course, not limited to plug-in or slipping or snatching connections as exemplified here. Any other suitable interconnection is also contemplated.

REFERENCE NUMERALS

1 implant
3 device
31 portion for folding and/or unfolding the implant
33 opening
5 catheter
51 cord of catheter
53 outer sheath
511a third section
511b fourth section
7 folding and/or unfolding means
71 portion of the folding and/or unfolding means
311a first section
311b second section
13 bearing
15 engagement
19 guiding structure
21 grooves
23 rib
35 outer sheath
37 outer surface
38 worm
39 attachment site
53 catheter sheath

What is claimed is:

1. A device releasably attachable or interconnectable with a foldable and unfoldable medical implant, the device being configured to be attached to or interconnected with a delivery device for implanting the implant, the device comprising:
    an outer portion;
    an inner portion housed within the outer portion for folding and unfolding the implant;
    folding and unfolding means comprising strings, reins, or threads for folding and unfolding the implant, wherein at least one portion of the folding and unfolding means is connected at an attachment portion with the inner portion of the device and wherein the inner portion is rotatably and concentrically supported within the outer portion of the device along a length of the inner portion, such that the inner portion is rotatable around a longitudinal axis of the device and during a rotation of the inner portion, the inner portion is configured to move in a longitudinal direction relative to the outer portion, and the folding and unfolding means are configured to be wound spirally or helically along the longitudinal axis around the inner portion within the outer portion during rotational and longitudinal movement of the inner portion.

2. A device according to claim 1, further comprising the implant, wherein the implant is detachable from the device.

3. A device according to claim 1, wherein the inner portion is rotatably supported by a bearing.

4. A device according to claim 1, further comprising an advancing mechanism or a displacing mechanism that enables a longitudinal displacement within the device of the inner portion, and that advances or displaces the inner portion in a longitudinal direction of the device when actuated.

5. A device according to claim 1, further comprising attaching or interconnecting means that comprises a first section, a second section, a third section and a fourth section for being attached or interconnected to a delivery device.

6. A device according to claim 5, wherein the attaching or interconnecting means comprises at least a first section that is rotatably supported within or on the device.

7. A device according to claim 5, wherein the attaching or interconnecting means comprises at least a second section that is arranged on the device in a manner such that the second section is not rotatable with respect to the device.

8. A device according to claim 1, wherein the inner portion comprises a guiding structure for guiding strings of the folding and unfolding means upon rotation of the inner portion.

9. A device according to claim 8, wherein the guiding structure comprises grooves wound spirally or helically along the longitudinal axis around the inner portion such that the folding and unfolding means are received in the grooves during winding up around the inner portion.

10. A device according to claim 1, being a catheter tip or a front end component of a catheter.

11. The device of claim 1, further comprising an attached delivery device.

12. A delivery device according to claim 11, further comprising attaching or interconnecting means that comprises a first section, a second section, a third section and a fourth section for attaching the delivery device to or interconnecting with the device.

13. A delivery device according to claim 12, wherein the attaching or interconnecting means for attaching the delivery device to the device includes the third section for interconnecting with the first section of the attaching or interconnecting means of the device.

14. A delivery device according to claim 13, wherein the attaching or interconnecting means for attaching the delivery device to the device comprise the fourth section for interconnecting with the second section of the attaching or interconnecting means of the device.

15. A delivery device according to claim 13, wherein the third section of the attaching or interconnecting means of the delivery device is rotatably arranged within the delivery device.

16. A delivery device according to claim 11, the delivery device being a flexible catheter.

17. A device according to claim 1, being a catheter tip.

18. A device according to claim 1, wherein
the outer portion includes a closed proximal end and an open distal end, the closed proximal end being disposed farther away from a handle of the delivery device than the open distal end, and
the inner portion is housed within the outer portion with an axial end of the inner portion and an inner surface of the closed proximal end of the outer portion facing each other.

19. The device according to claim 1,
wherein one of the outer portion and the inner portion comprises engagements,
the other one of the outer portion and the inner portion comprises a worm or thread, and
the worm or thread and the engagements are engaged with each other to provide a mechanism for effecting a longitudinal displacement of the inner portion relative to the outer portion with the rotational movement.

20. A method of providing a delivery implement with a device according to claim 1 and an implant before implantation, the method comprising the step:
attaching or fixing the device comprising the implant onto the delivery implement.

21. A method according to claim 20, wherein the device is attached or fixed to the delivery device in the operation room.

* * * * *